(12) United States Patent
Jacobs et al.

(10) Patent No.: US 8,507,280 B2
(45) Date of Patent: Aug. 13, 2013

(54) METHOD OF NORMALIZING SURFACE TENSION OF A SAMPLE FLUID

(75) Inventors: Merrit Jacobs, Fairport, NY (US); Ed Graham, Penfield, NY (US); Karen Vavra, Rochester, NY (US); Chuck Noeson, Rochester, NY (US); Susan Danielson, Honeoye Falls, NY (US); Terri Fazio, Rochester, NY (US)

(73) Assignee: Ortho-Clinical Diagnostics, Inc., Raritan, NJ (US)

( * ) Notice: Subject to any disclaimer, the term of this patent is extended or adjusted under 35 U.S.C. 154(b) by 1290 days.

(21) Appl. No.: 11/838,576

(22) Filed: Aug. 14, 2007

(65) Prior Publication Data

US 2008/0044908 A1 Feb. 21, 2008

Related U.S. Application Data

(60) Provisional application No. 60/822,895, filed on Aug. 18, 2006.

(51) Int. Cl.
*G01N 35/00* (2006.01)
*G01N 1/00* (2006.01)

(52) U.S. Cl.
USPC ............... 436/49; 436/43; 436/174; 436/180

(58) Field of Classification Search
None
See application file for complete search history.

(56) References Cited

U.S. PATENT DOCUMENTS

| | | | |
|---|---|---|---|
| 5,753,451 A * | 5/1998 | Smith | 435/12 |
| 6,455,288 B1 * | 9/2002 | Jakobovits et al. | 435/190 |
| 6,797,518 B1 | 9/2004 | Jacobs et al. | |
| 2003/0003591 A1 | 1/2003 | LaCourt et al. | |
| 2003/0022380 A1 * | 1/2003 | Jakubowicz et al. | 436/54 |
| 2003/0026733 A1 | 2/2003 | LaCourt et al. | |
| 2003/0181826 A1 | 9/2003 | Smith et al. | |
| 2003/0219890 A1 * | 11/2003 | Gordon et al. | 435/287.2 |

FOREIGN PATENT DOCUMENTS

| | | |
|---|---|---|
| EP | 1 382 393 A2 | 1/2004 |
| JP | 05 196620 A | 8/1993 |
| JP | 2004 325422 A | 11/2004 |

OTHER PUBLICATIONS

Yeh, Carol Kuei-Jyum et al. "Co-surfactant of ethoxylated sorbitan ester and sorbitan monooleate for enhanced flushing of tetrachloroethylene." Chemosphere (2002) 49 421-430.*

* cited by examiner

*Primary Examiner* — Yelena G Gakh
*Assistant Examiner* — Christopher A Hixson

(57) ABSTRACT

A method of normalizing surface tension of a sample fluid on a clinical analyzer is disclosed. The method comprises aspirating a portion of a sample fluid into a metering tip, the metering tip having a lower end through which the sample fluid is aspirated and an upper end; sealing the lower end of the metering tip, forming a cuvette for the portion of the sample fluid; pre-treating a micro-tip with a surface tension-normalizing agent, and then dispensing the surface tension-normalizing agent into the sample fluid in the cuvette; mixing the surface tension-normalizing agent and the sample fluid in the cuvette using the micro-tip to create a mixture of the sample fluid and the surface tension-normalizing agent, the mixture having a normalized surface tension; and using the mixture for testing on the clinical analyzer.

15 Claims, 12 Drawing Sheets

METHOD OF NORMALIZING SURFACE TENSION OF A SAMPLE FLUID

CROSS-REFERENCE TO RELATED APPLICATIONS

This application claims the benefit of U.S. Provisional Application No. 60/822,895, filed Aug. 18, 2006.

STATEMENT REGARDING FEDERALLY SPONSORED RESEARCH OR DEVELOPMENT

Not applicable.

FIELD OF THE INVENTION

The invention relates to the field of clinical analyzers, and more particularly to a novel method for normalizing surface tension of a sample fluid being run on a clinical analyzer.

BACKGROUND OF THE INVENTION

Clinical analyzers generally utilize dry chemistry systems and/or wet chemistry systems. Each chemistry system is somewhat unique in terms of its operation. For example, known "dry" chemistry systems typically include a sample supply which includes a number of sample containers, a metering/transport mechanism, and an incubator having a plurality of test read stations. A quantity of sample is aspirated into a metering tip using a proboscis or probe carried by a movable metering truck along a transport rail. A quantity of sample from the tip is then metered (dispensed) onto a dry slide element which is loaded into the incubator. The slide element is incubated and optical or other reads are taken for analyte detection.

A "wet" chemistry system on the other hand, utilizes a reaction vessel such as a cuvette, into which quantities of patient sample, at least one reagent fluid, and/or other fluids are combined for conducting an assay. The assay is also incubated and tests are conducted for analyte detection. The "wet" chemistry system also includes a metering mechanism to transport patient sample fluid from the sample supply to the reaction vessel.

A number of known clinical analyzers incorporate both wet and dry chemistry systems in a single apparatus, and are known as "combinational" clinical analyzers.

When operating clinical analyzers, various problems can be encountered. For example, the sample volume that the analyzer delivers to the reaction cell may vary by sample/patient. In addition, some analytes may have reduced recovery and the recovery may vary by sample/patient. Both of these issues result in what an end user would observe as random bias. Customers usually relate to this error as the lack of fit to a regression line compared to a reference method. In addition, certain controls and proficiency fluids may show lower predictions on a particular analyzer compared to other systems.

A need exists for methods which can overcome these problems and improve the accuracy and consistency of clinical analyzers.

BRIEF SUMMARY OF THE INVENTION

To this end, investigation into the causes of these problems shows that the random error in sample volume is driven predominantly by the variability in the sample fluid surface tensions. The random error in the recovery is driven in part by the random error in volume but for some assays there is also a loss in the analyte being measured because the analyte tends to stick to the plastic surfaces as the analyzer processes it.

The subject invention provides a method which overcomes these problems by normalizing surface tension of a sample fluid on a clinical analyzer. The method uses a surface tension-reducing agent, which may also block adhesion of analytes to plastic and which may also improve metering performance of the clinical analyzer. In a preferred embodiment, the method comprises:

aspirating a portion of a sample fluid into a metering tip, the metering tip having a lower end through which the sample fluid is aspirated and an upper end;

sealing the lower end of the metering tip, forming a cuvette for the portion of the sample fluid;

pre-treating a micro-tip with a surface tension-normalizing agent, and then dispensing the surface tension-normalizing agent into the sample fluid in the cuvette;

mixing the surface tension-normalizing agent and the sample fluid in the cuvette using the micro-tip to create a mixture of the sample fluid and the surface tension-normalizing agent, the mixture having a normalized surface tension; and using the mixture for testing on the clinical analyzer.

The method of the subject invention overcomes the above problems of prior analyzers, without adulterating the original sample fluid and without substantially slowing down the throughput of the analyzer. Additional features and advantages of the subject invention will be apparent from the description which follows when considered in conjunction with the attached figures.

DETAILED DESCRIPTION OF THE INVENTION

The following description relates to a combinational (i.e., wet/dry) clinical analyzer that is used for the testing of biological samples, such as urine, whole blood, serum, or plasma, preferably human patient samples. The invention is then described in the context of this particular analyzer. It should be readily apparent to those of ordinary skill in the art that the method of the subject invention can also be practiced on analyzers of other configurations that can readily be adapted to the method disclosed herein. For example, the analyzer could include a pair of wet chemistry systems or only a wet chemistry system.

By "combinational" it is meant that the analyzer includes at least two chemistry systems which can encompass any combination of "dry" and/or "wet" chemistry systems. In brief and in a typical "dry" chemistry system, a patient sample and/or other fluids are aspirated from a fluid supply and deposited onto a dry slide element such as those described in U.S. Pat. No. 3,992,158 to Przyblyowicz et al. The dry slide element is incubated and the amount or presence of at least one analyte in the sample metered onto the element is determined, such as through use of an electrometer, reflectometer or other suitable testing device.

A "wet" chemistry system for purposes of the description which follows includes a reaction vessel which receives predetermined volumetric quantities of sample, reagent, and other fluids which are appropriately metered into the reaction vessel in order to perform an assay(s). The assay is incubated as the fluids are added to the assay(s) and specific analysis is performed, such as through luminescence, light transmissivity, photon detection, and the like using suitable testing apparatus.

Several other terms are used throughout the discussion including the terms "metering tips" and "micro-tips". For purposes of this description, a metering tip refers to a fluid aspirating/dispensing member which can be attached to a proboscis as used in a metering mechanism. The tip includes an open top end and a bottom dispense end and is capable of retaining a volumetric quantity of fluid. Metering tips in and of themselves are well known in the field. A "micro-tip" for purposes of this discussion refers to a metering tip which fits the definitional requirements set forth above. In addition, this tip is sized to retain a smaller (micro) volume of fluid. Moreover, the micro-tip can be fitted within the confines of the metering tip for advantages which will be apparent below.

Figure 1:
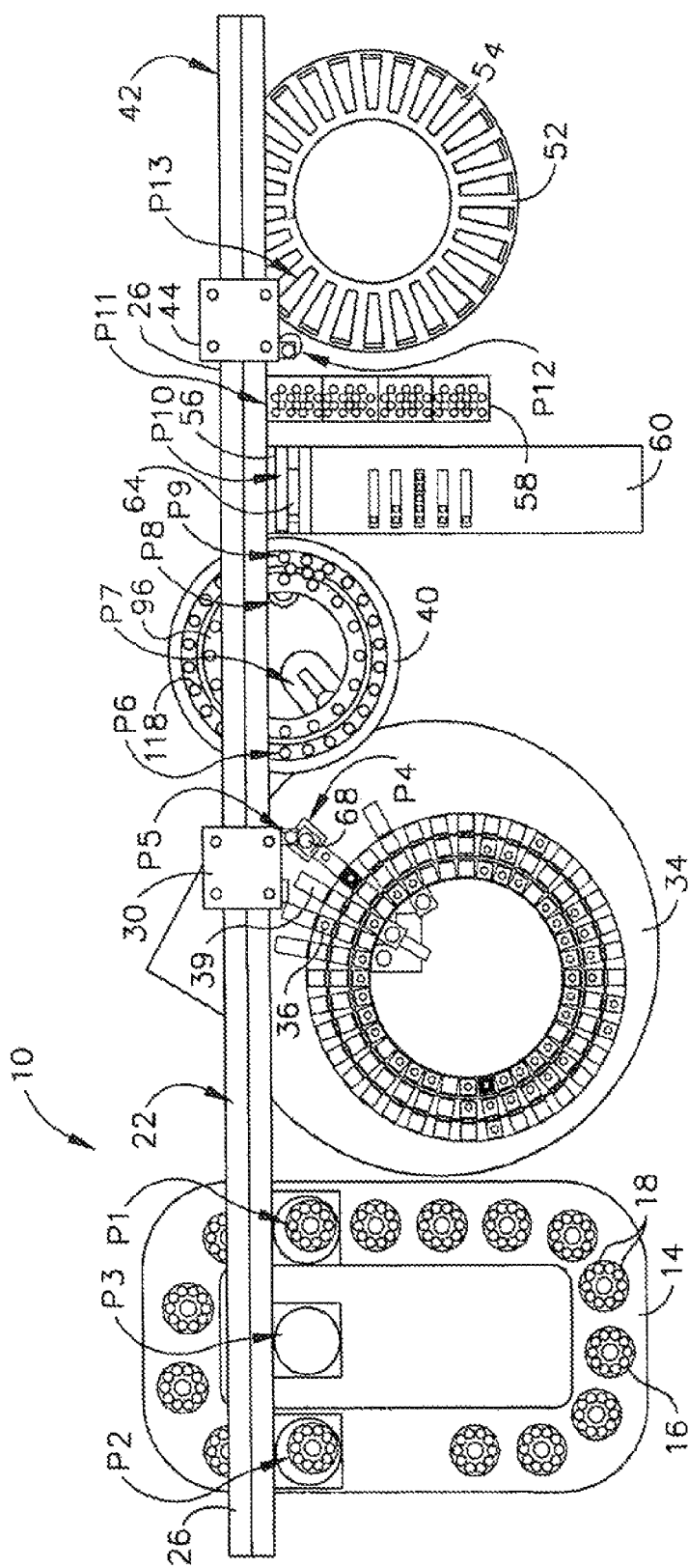
FIG. 1 is an operational block diagram of a combinational wet/dry clinical analyzer including a plurality of stations that interact with a metering system.

Referring to FIG. 1, there is shown an automated combinational clinical analyzer 10 having a number of component systems which are briefly discussed to provide adequate background for the invention. The analyzer 10 includes a primary sample handler 14 that retains a plurality of primary sample containers 18, a primary metering mechanism 22 which includes a metering transport rail 26 and a metering truck 30 which is movable along the transport rail between a number of stations. Among the stations disposed along the travel path of the metering mechanism 22 are a metering station 68 for a first incubator assembly 34. At the metering station 68, a quantity of sample can be deposited onto a dry slide element which is then shuttled into the incubator assembly 34. The incubator assembly 34 includes at least one read station including a testing device for correlated analyte detection, such as reflectometer (not shown) or an electrometer (not shown). The preceding components each comprise a dry chemistry system for the herein described automated combinational analyzer 10.

Still referring to FIG. 1, the analyzer 10 further includes a secondary metering mechanism 42 that includes a metering truck 44 which is also movable along the metering transport rail 26, a reagent wheel 52 which includes a plurality of containers of at least one reagent fluid, a second incubator assembly 56, a micro-tip supply 58, and a reaction vessel conveyor 60 which carries a plurality of reaction vessels 64. These components have merely been listed in this portion of the discussion. Details relating to their features will be additionally supplied in a later portion of the discussion. For purposes of this description, however, each of the above-noted components define a wet chemistry system for the herein described combinational analyzer 10.

As introduced above, the primary metering mechanism 22 and the secondary metering mechanism 42 travel among a number of stations of the analyzer 10. Each of these stations is defined as a metering stopping point for the metering truck 30 and 44 respectively. By way of example, and in no particular order of significance or priority, these metering stopping points include for example: a primary metering point (P1) for the initial aspiration of sample by the primary metering mechanism 22; a reflex metering point (P2) where additional aspirates of sample can be taken if needed, i.e. for dilution purposes, etc.; a priority handling or STAT metering point (P3) for introducing priority/STAT samples; a thin film metering point (P4) where the slide element 36 is spotted with sample fluid; a tip seal point (P5) for sealing a lower end 105 of a metering tip 102 (see FIG. 10) at the tip sealer 142 for forming a cuvette ("cuvetip"); a first tip pick-up point (P6) where the primary metering mechanism 22 obtains a new metering tip 102; a first tip eject point (P7) where the primary metering mechanism 22 drops off a used metering tip 102 or sealed tip 102 after testing has been completed; a second cuvette metering point (P8) where the secondary metering mechanism 42 meters samples from a cuvetip; a second tip pick-up point (P9) where the primary metering mechanism 22 obtains another new metering tip 102; a cuvette metering point (P10) where the secondary metering system meters into a wet cuvette (traditional type); a micro-tip pick-up point (P11) where the secondary metering mechanism 42 picks up new microtips 107; a second tip eject point (P12) where the secondary metering mechanism 42 deposits used microtips; and a wet reagent metering point (P13) where the secondary metering mechanism 42 aspirates wet reagent at the reagent wheel 52.

As will be described in greater detail later in the disclosure, these stations or points (P1-P13) are illustrative of the various points interacted on by the metering mechanisms 22 and 42 respectively.

Still referring to FIG. 1, a sample aliquot handler apparatus 40 is disposed in spaced relation between the first incubator assembly 34 of the dry chemistry system and the second incubator assembly 56 of the wet chemistry system of the above-described analyzer 10. The following discussion pertains to a specific description of the sample aliquot handler 40 followed by the operational details of the sample handler in conjunction with the wet and dry chemistry systems of the herein described combinational analyzer 10.

First, and as shown in FIGS. 1-3 and 5, the sample aliquot handler 40 includes a circular cylindrical housing 80 having a cover 84. The housing is defined by an interior sized for containing a number of retained components which include an inner rotor assembly 88 (not shown in FIG. 2), a pair of position sensors 126, 128, and a tip removing assembly 122. Each of the above-noted components are attached to an interior facing surface of a bottom mounting plate 138 of the housing 80. In addition, an outer rotor assembly 92 is supported at the top of the housing 80, the outer rotor assembly being disposed outside the periphery of the cover 84.

Figure 3:
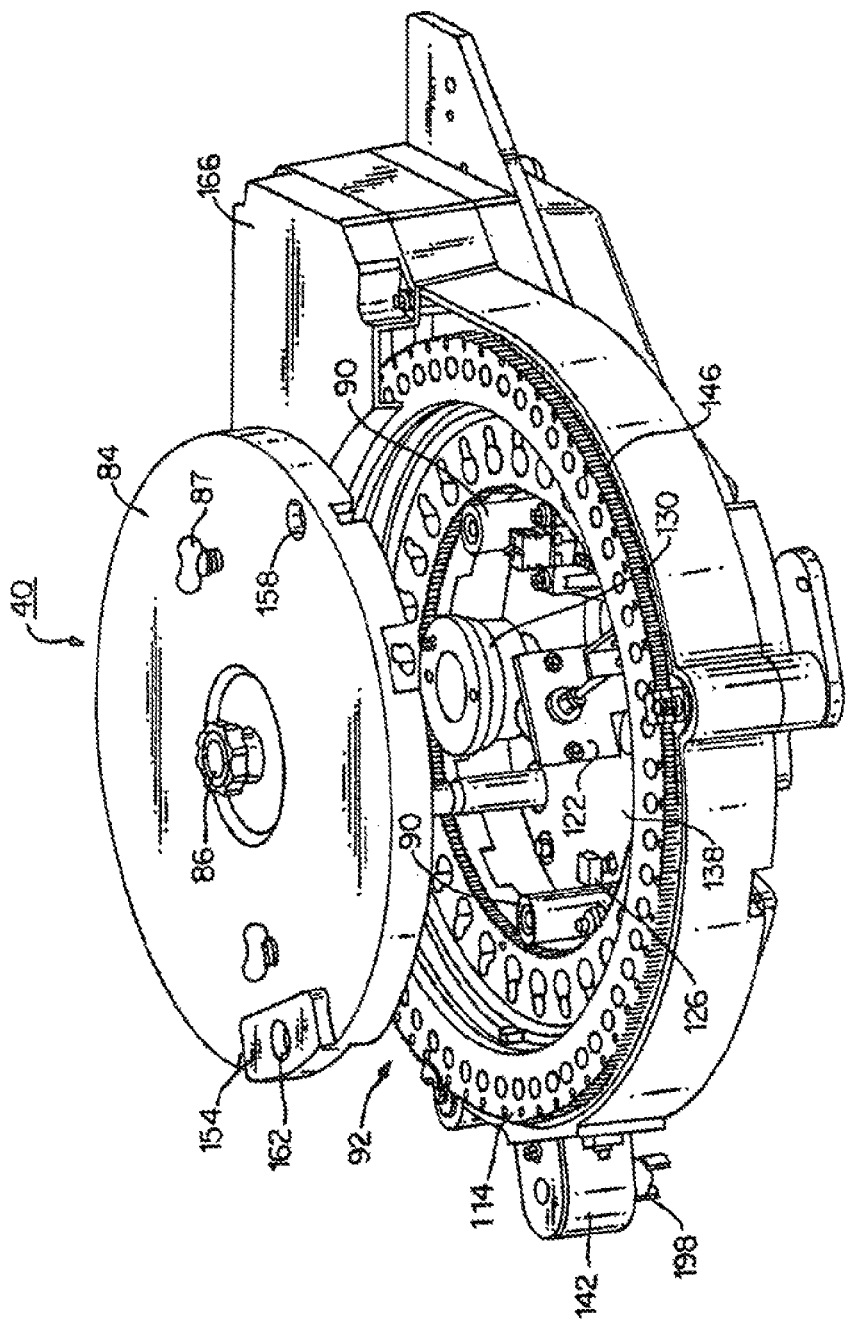
FIG. 3 is a partially exploded top perspective view of the sample aliquot handler of FIGS. 1 and 2.
Figure 4:
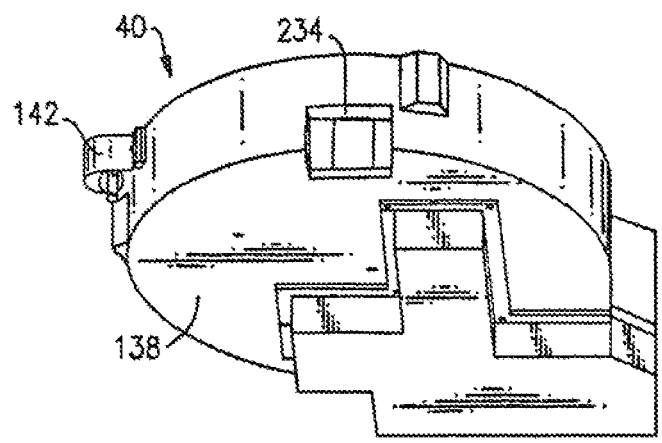
FIG. 4 is a bottom view of the sample aliquot handler of FIGS. 1-3.
Figure 5:
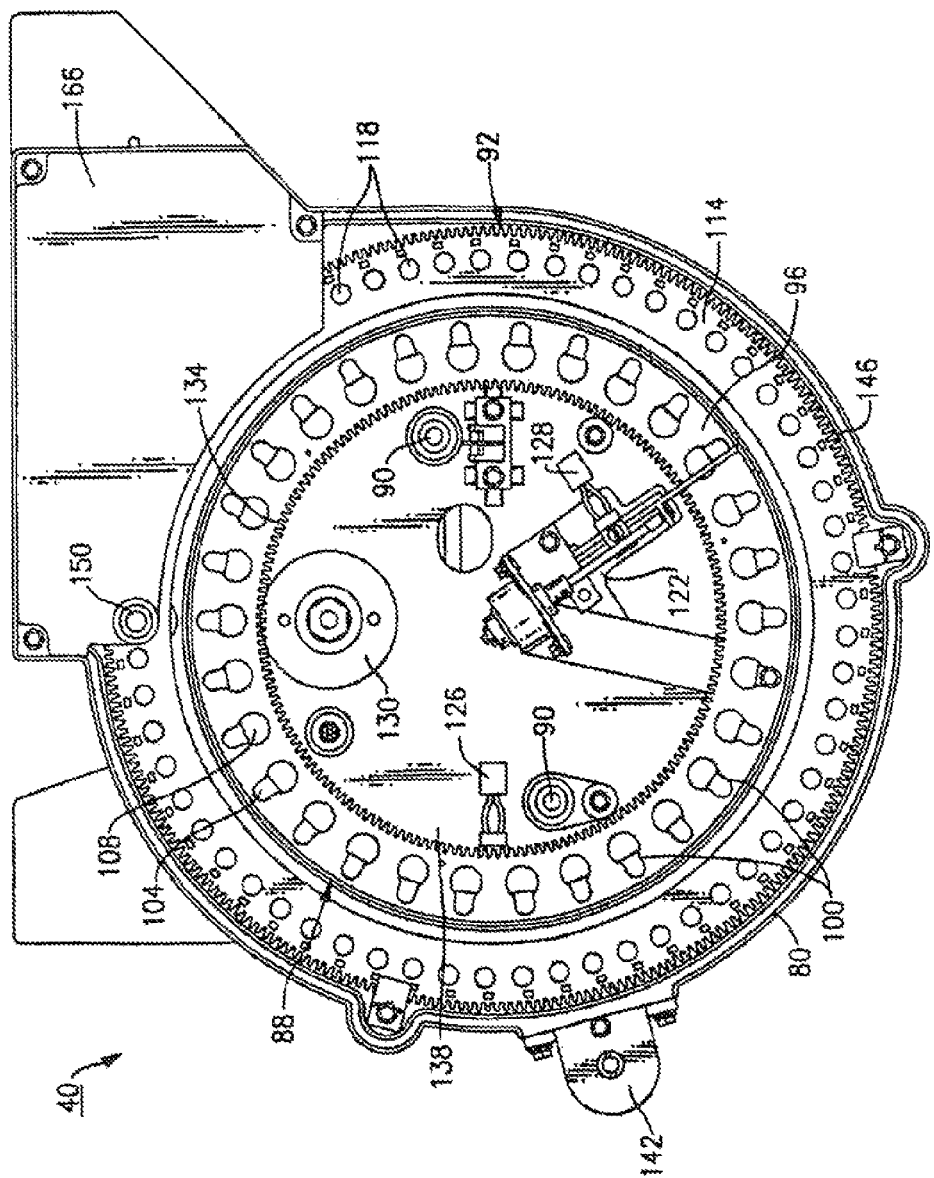
FIG. 5 is a top plan view of the sample aliquot handler of FIGS. 1-4.
Figure 8:
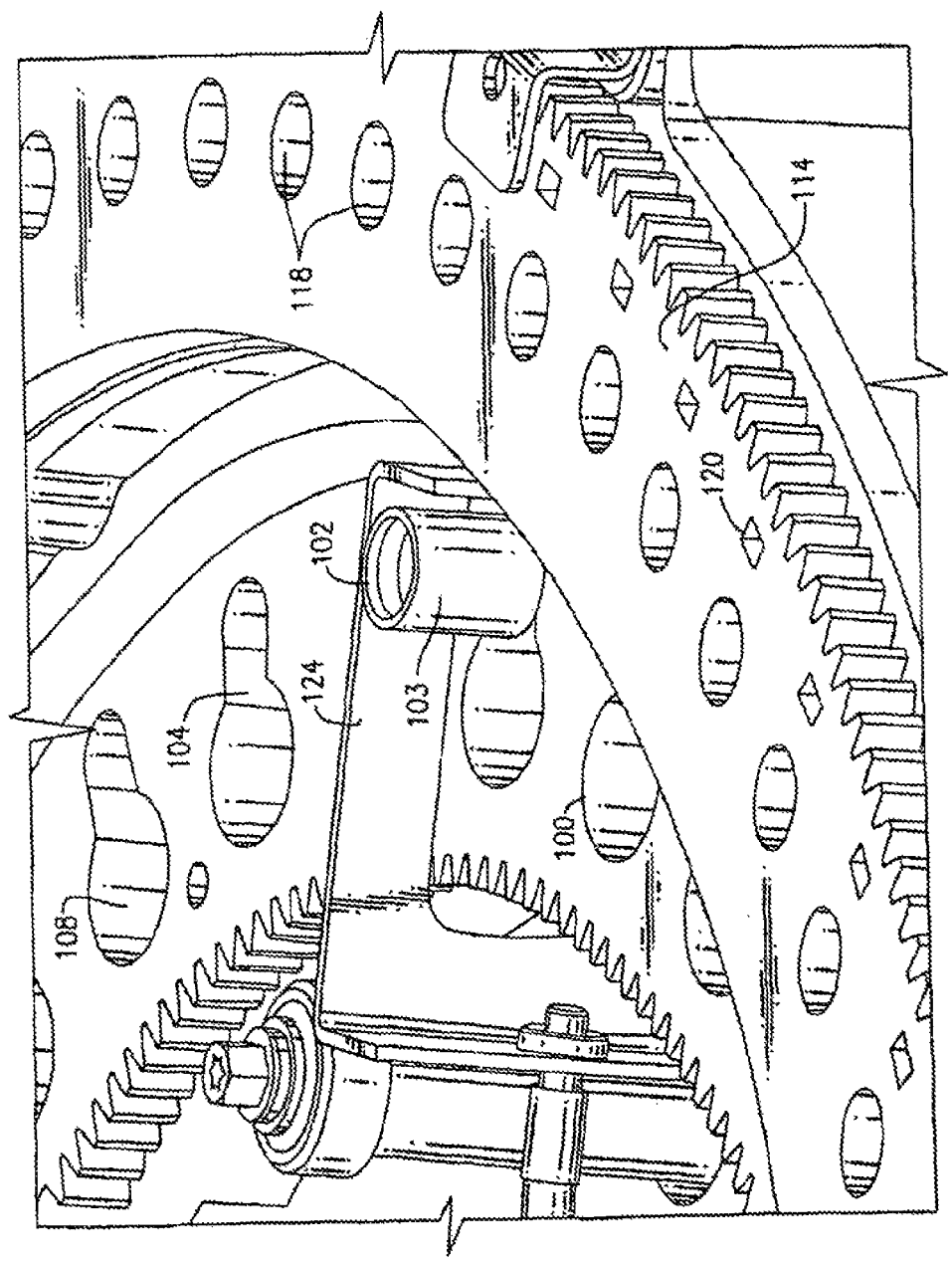
FIG. 8 is an enlarged partial top perspective view of the sample aliquot handler of FIGS. 1-7 showing the removal of a sealed metering tip from the handler to a dump station.

A pair of stanchions 90 also extending from the interior facing surface of the mounting plate 138 assist in supporting the cover 84 which covers the inner rotor assembly 88. The cover 84 further includes a center handle 86, as well as a pair of opposing twist fasteners 87 which engage corresponding openings provided in the stanchions 90. The cover 84 also includes a tip stripping assembly 154 that is described in greater detail below. The following relates to a more detailed discussion of the inner and outer rotor assemblies 88, 92. Referring to FIGS. 3, 5, and 8, the inner rotor assembly 88 includes a rotatable circular ring member 96, which is rotatably driven about a center axis of rotation by means of a gear drive mechanism. The drive mechanism includes a motor having a rotating engagement portion 130 which extends above the interior facing surface of the mounting plate 138. A set of linear gear teeth 134 are provided on an inner edge of the ring member 96 which mesh with the engagement portion 130. The ring member 96 of the inner rotor assembly 88 further includes a plurality of sample container supply stations 100, each of the stations being circumferentially disposed about the periphery of the ring member. Each of the sample container supply stations 100 are defined by a slotted outer opening 104 which is linked to a radially adjacent and contiguous inner opening 108. The size of the inner opening 108 is much larger than that of the slotted outer opening 104 for reasons which will be become apparent below. According to this specific embodiment, (30) thirty sample container supply stations 100 are provided on the inner ring member 96, though it should be readily apparent that this parameter can be easily varied.

Referring now to FIGS. 2, 3, 5, and 8, and as noted above, the outer rotor assembly 92 of the sample aliquot handler 40 extends outside the periphery of the cover 84. This assembly is comprised of a circular support ring 114 having a plurality of circular circumferentially disposed tip supply stations 118 which are equally spaced about the periphery of the ring. Like the inner rotor assembly 88, a gear drive mechanism is used to rotatably drive the ring. A set of linear gear teeth 146 provided on an outer edge of the support ring 114 are engaged by the engagement portion (not shown) of a motor (not shown) to cause rotation of the support ring 114. It should be pointed out that the above described gear drive mechanisms are exemplary. That is, other drive mechanisms can be employed to cause rotational movement of either the support ring 114 or the ring member 96.

The support ring 114 and the ring member 96 of the outer rotor assembly 92 and inner rotor assembly 88, respectively, are concentric, the rotating components of each assembly being independently driven by their respective gear drive mechanisms about a common axis of rotation.

According to this embodiment, the support ring 114 of the outer rotor assembly 92 further includes a series of circumferentially spaced slots 120, FIG. 8, disposed on an outer periphery of the ring for aiding in the initial angular positioning of the ring during assembly.

Figure 9:
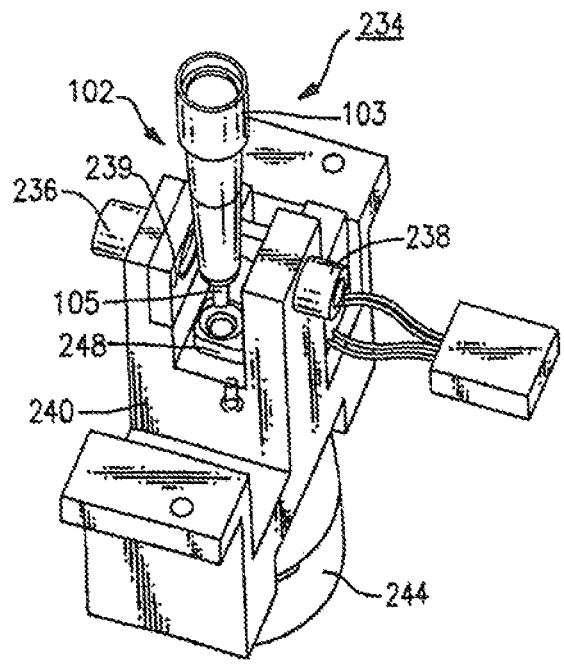
FIGS. 9 and 10 are partial side elevational views illustrating a sample integrity read station for the sample aliquot handler of FIGS. 1-8.

Still referring to FIGS. 2, 3, 5 and 8, each of the tip supply stations 118 of the support ring 114 of the outer rotor assembly 92 are circular openings which are sized to receive a metering tip 102, FIG. 9, 10, from a tip supply (not shown) at a tip deposit station 150 provided as an opening in an adjacent cover 166 covering the drive motor (not shown) for the rotatable support ring 114 of the outer rotor assembly 92. According to this embodiment, a total of sixty (60) equally spaced tip supply stations 118 are provided, though it should be apparent, as previously noted above, that this parameter can be suitably varied.

According to this specific embodiment, each of the sample container supply stations 100 and the tip supply stations 118 of the inner rotor and outer rotor assemblies 88, 92, respectively, are sized to receive a fluid aspirating/dispensing member. According to this embodiment, the fluid aspirating/dispensing member is a metering tip 102, shown in FIGS. 9 and 10, which includes an open upper end 103 and a lower dispense end 105 through which liquid can be dispensed. More specifically, the metering tip described herein is a disposable plastic member made from polypropylene or other plastic moldable material, such as the metering tip manufactured by the Johnson & Johnson Company under the trade name of Vitros™, though it will be apparent that other fluid dispensing/aspirating members can be substituted.

Referring to FIGS. 2-6, the sample aliquot handler 40 includes a tip sealer 142 which is mounted by conventional means, such as threaded fasteners, to the exterior of the housing 80.

Figure 6:
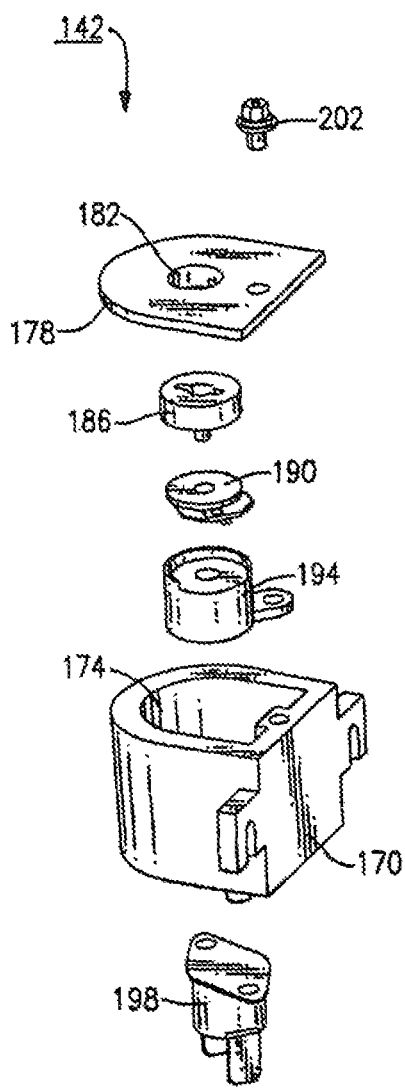
FIG. 6 is an exploded top perspective view of a tip sealer used in connection with the sample aliquot handler of FIGS. 1-5.

Referring more particularly to FIG. 6, the tip sealer 142 includes a housing 170 which is mounted to the exterior of the handler housing 80, FIG. 3, the housing having a defined interior 174 and a cover 178 which covers the top end of the housing held in place by fastener 202. A number of components are contained within the sealer housing 170 including a cylindrical support 194, and a heating element assembly 190, which is placed in a recess of the support within a bottom portion of an anvil 186. The heating element assembly 190 includes a resistive type heater and a control thermistor. The cover 178 includes a center opening 182 which is sized to permit passage of a metering tip 102, FIG. 9, such that the opening of the dispense end 105 of the tip can be sealed through engagement with the heated anvil 186. A safety thermostat 198 attached to the bottom of the housing 170 automatically shuts down the tip sealer 142 if a predetermined temperature is reached to prevent overheating. Further details relating to the sealing of metering tips in this manner is described in commonly owned U.S. Pat. No. 6,797,518, issued Sep. 28, 2004, of Jacobs et al., entitled ANALYSIS METHOD WITH SAMPLE QUALITY MEASUREMENT, the entire contents of which are incorporated herein by reference.

Figure 7:
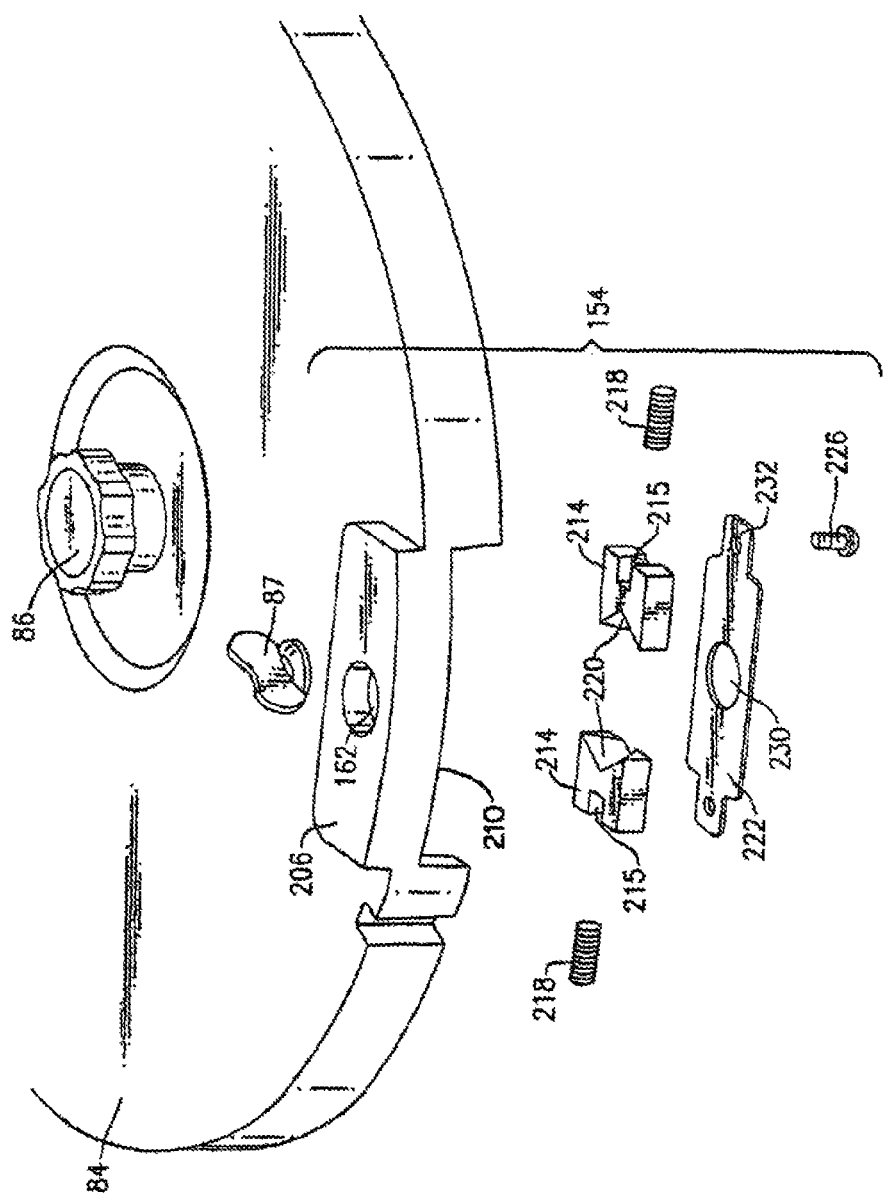
FIG. 7 is a partial top perspective of the cover of the sample aliquot handler of FIGS. 1-6 showing an exploded view of a tip stripper.

Referring to FIG. 7, the sample aliquot handler 40 further includes a tip stripping assembly 154 that is provided within a recessed portion 210 of the bottom of the cover 84. A pair of V-blocks 214 are biasedly maintained in a first or "home" position by a pair of compression springs 218 within respective slotted regions 215. The V-blocks 214 are biased in order to create a predetermined gap between a pair of tapered surfaces 220. The cover 84 includes an opening 162 within a raised portion 206, which is aligned with the gap of the V-blocks 214 to permit passage there through of a metering tip 102, FIG. 9. A retaining plate 222 used to support the components of the tip stripping assembly 154 is secured to the bottom of the cover 84 using fasteners 226 (only one being shown in FIG. 7) which extend through corresponding holes 232 formed in the retaining plate. Hole 230 permits the metering tip 102 to be dropped into an empty sample container supply position 100 of the circular ring 96 of the inner rotor assembly 88.

Figure 10:
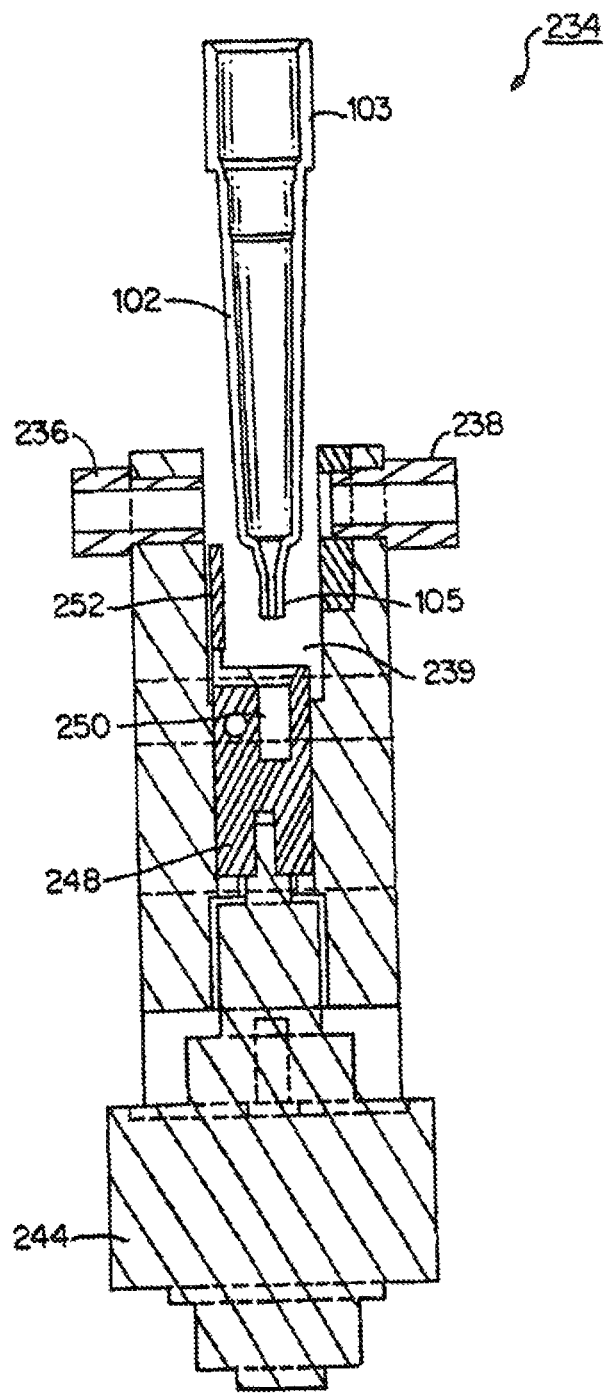

Referring to FIGS. 9 and 10, a sample integrity read station 234 includes a station housing 240 and an optical reading device, such as a spectrophotometer which includes receiving and transmitting optics 236, 238 disposed on opposite sides of a test slot or cavity 239. A linear actuator 244 is disposed at the bottom of the station housing 240, the actuator having an engagement member 248 attached thereto which is vertically movable and includes a tip receiving cavity 250 and a vertically extending flag 252. The actuator 244 and engagement member 248 together form a lift mechanism that aligns the fluid contents of a retained metering tip 102 with the receiving and transmitting optics 236, 238 of the spectrophotometer. The housing 240 of the sample integrity read station 234 is stationarily positioned to the mounting plate 138 beneath a predetermined angular position of the circular ring 96 and the cavity 239 is aligned with the sample container supply stations 100, FIG. 5. As described below, the sample integrity read station 234 provides spectrophotometric analysis of the sample contents of a sealed metering tip 102 in order to ascertain the presence of certain sera components, such as hemoglobin, albumin, lipoproteins etc.

Referring to FIG. 1, and with respect to the remaining components of the present analyzer 10, the second incubator assembly 56 is positioned adjacent to the sample aliquot handler apparatus 40. The second incubator assembly 56 is sized to receive at least one reaction vessel 64 and includes a read station (not shown) including a testing device, such as a spectrophotometer, for detecting the presence or amount of an analyte in a sample.

Each reaction vessel 64 is conveyed in relation to the second incubator assembly 56 and a metering station for receiving sample from sealed metering tips 102 within the sample aliquot handler apparatus 40 and at least one reagent from the reagent wheel 52.

Figure 2:
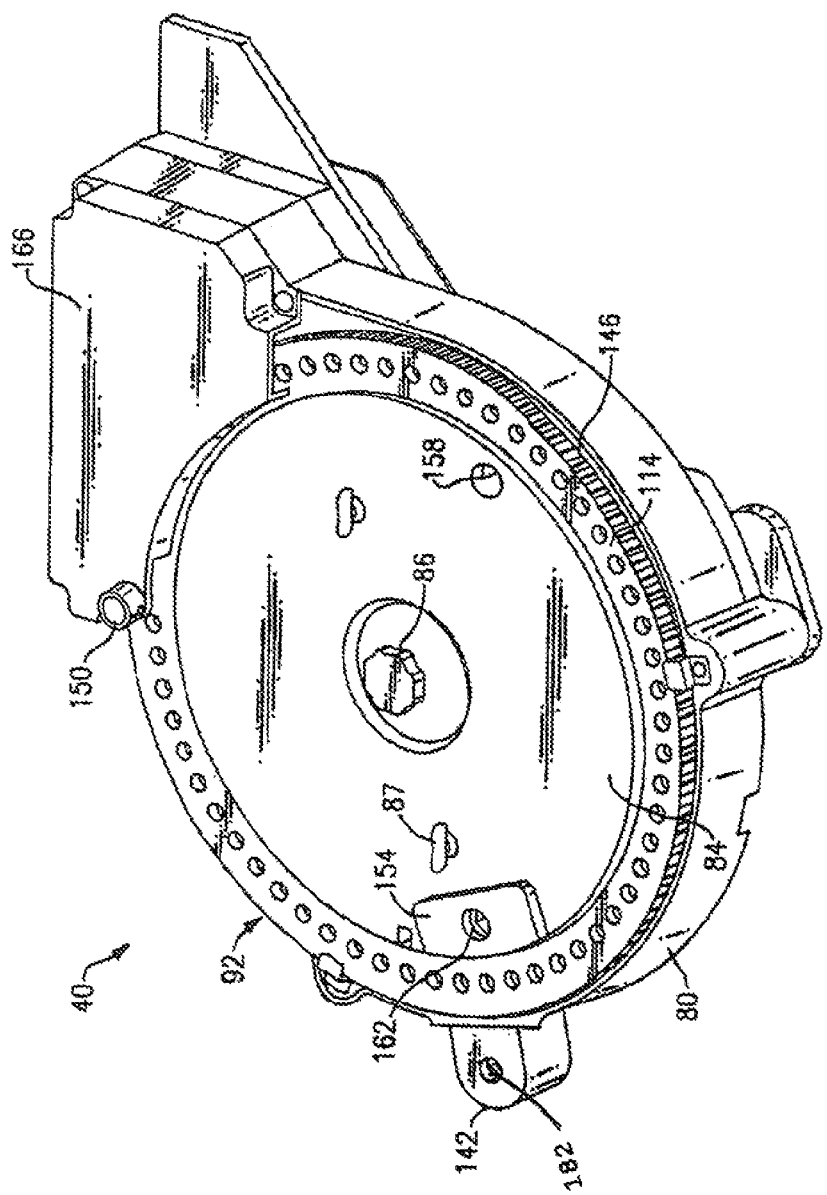
FIG. 2 is a top perspective view of the sample aliquot handler of FIG. 1.
Figure 13:
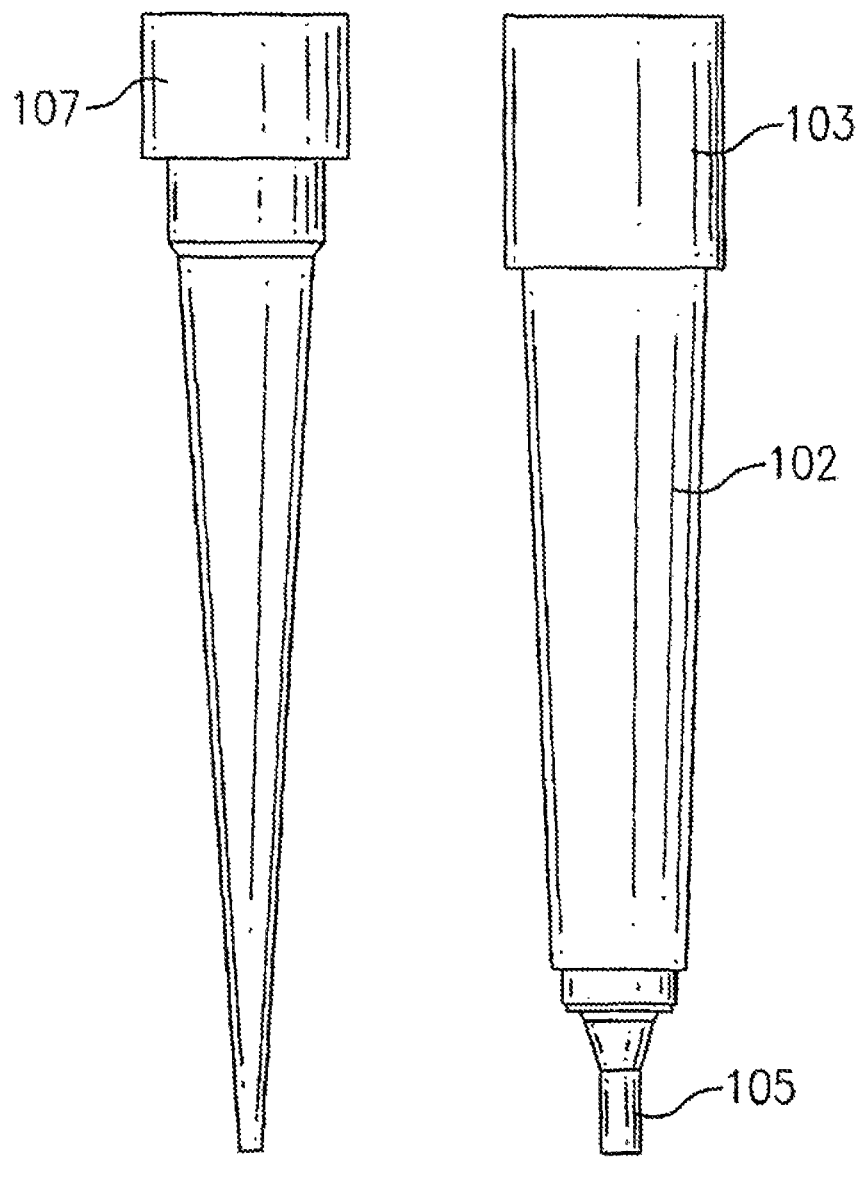
FIG. 13 is a side elevational view of a pair of disposable tips, a metering tip and a micro-tip, used in conjunction with the chemical analyzer of FIGS. 1-12.

The micro-tip supply 58 conveys a plurality of disposable plastic micro-tips 107, FIG. 13, in which each of the tips are smaller than the sealed sample-containing metering tips 102, that are retained within the sample aliquot handler apparatus 40, as shown in FIGS. 2 and 3. The micro-tips 107 are retained in packages which are conveyed to a pickup station which is aligned with the metering truck 44 of the wet chemistry system of the herein described analyzer 10.

Each of the reaction vessels 64 includes a plurality of spaced reaction chambers for conducting a wet assay. A preferred version is described in commonly owned U.S. Patent Pub. No. US 2003/0003591 of LaCourt et al. entitled "Reaction Vessel", the contents of which are herein incorporated by reference. The reaction chambers can be provided for single (disposable) as well as for multiple use, according to the present invention. The vessels 64 of the present embodiment further include windows (not shown) on opposing sides of each reaction chamber which permit testing of the contents by means of a testing device, such as a spectrophotometer (not shown) which is included in a testing chamber which is disposed adjacent to the second incubator assembly 56. It will apparent, however, that other forms of reaction containment devices, such as reaction wells, cuvettes, test tubes, and even thin film or dry slide elements can be substituted.

The rotatable reagent wheel 52 includes a plurality of reagent containers or packs 54 each being disposed within appropriately sized slotted portions of a rotatable ring component. Each of the reagent packs 54 contain at least one and preferably two separately housed reagents within an injection molded structure, the packs being driven by a suitable drive mechanism along a circular path wherein the packs are stored for access and rotated to an appropriate position for aspiration. The reagent packs 54 can be loaded individually through a slot (not shown) in a cover (not shown) of the reagent wheel, the wheel further including a cooler (not shown) which maintains the reagents at an appropriate temperature and humidity.

As will now be more clearly described, the above-described sample aliquot handler 40 is used to asynchronously link the dry chemistry and wet chemistry systems of the combinational clinical analyzer 10. Having completed the description of the individual features and subassemblies of the clinical analyzer 10, details relating to the operation of the clinical analyzer are now provided.

Initially, a plurality of unsealed metering tips 102 are loaded one at a time as fed from a tip supply (not shown) through the opening that defines the tip deposit station 150 and are dropped into empty tip supply stations 118 provided on the support ring 114 of the outer rotor assembly 92. The support ring 114 is rotated incrementally by means of the gear drive mechanism (not shown) in order to align empty tip supply stations 118 into proper alignment with the tip deposit station 150.

As previously noted, the primary sample handler 14 contains a plurality of patient sample containers 18 which are movably disposed on rotatable sample trays 16. Details relating to the primary sample handler 14 and movement of the sample containers 18 are commonly known to those of ordinary skill in the field and do not form an essential part of the invention. Briefly, the sample containers 18 are generally tubular in shape and are disposed on rotatable sample trays 16 disposed on a drive belt or other support. The sample trays 16 are typically carousels which retain a plurality of the tubular sample containers 18, the trays being incremented about an elliptically shaped track by means of a drive mechanism (not shown) such as a magnetic drive, belt, or other known means into alignment with the metering transport rail 26.

As noted above, the metering transport rail 26 is aligned with the primary sample handler 14 and the auxiliary sample handler 40 such that a metering tip 102, FIG. 9, can be attached onto a proboscis (not shown) of the movable metering truck 30 of the primary metering mechanism 22 from a predetermined tip supply station 118.

The metering truck 30 is then shuttled along the transport rail 26 to the primary sample handler 14 and a volume of sample is drawn under vacuum and is aspirated from one of the patient sample containers 18 into the metering tip 102, FIGS. 9 and 10. Specific details relating to the attachment of a metering tip to a proboscis as well as details relating to the aspiration and metering of sample and other fluids are commonly known to those in the field. An example is provided, for example, in U.S. Pat. No. 4,340,390 to Collins et al., the entire contents of which are herein incorporated by reference.

Figure 11:
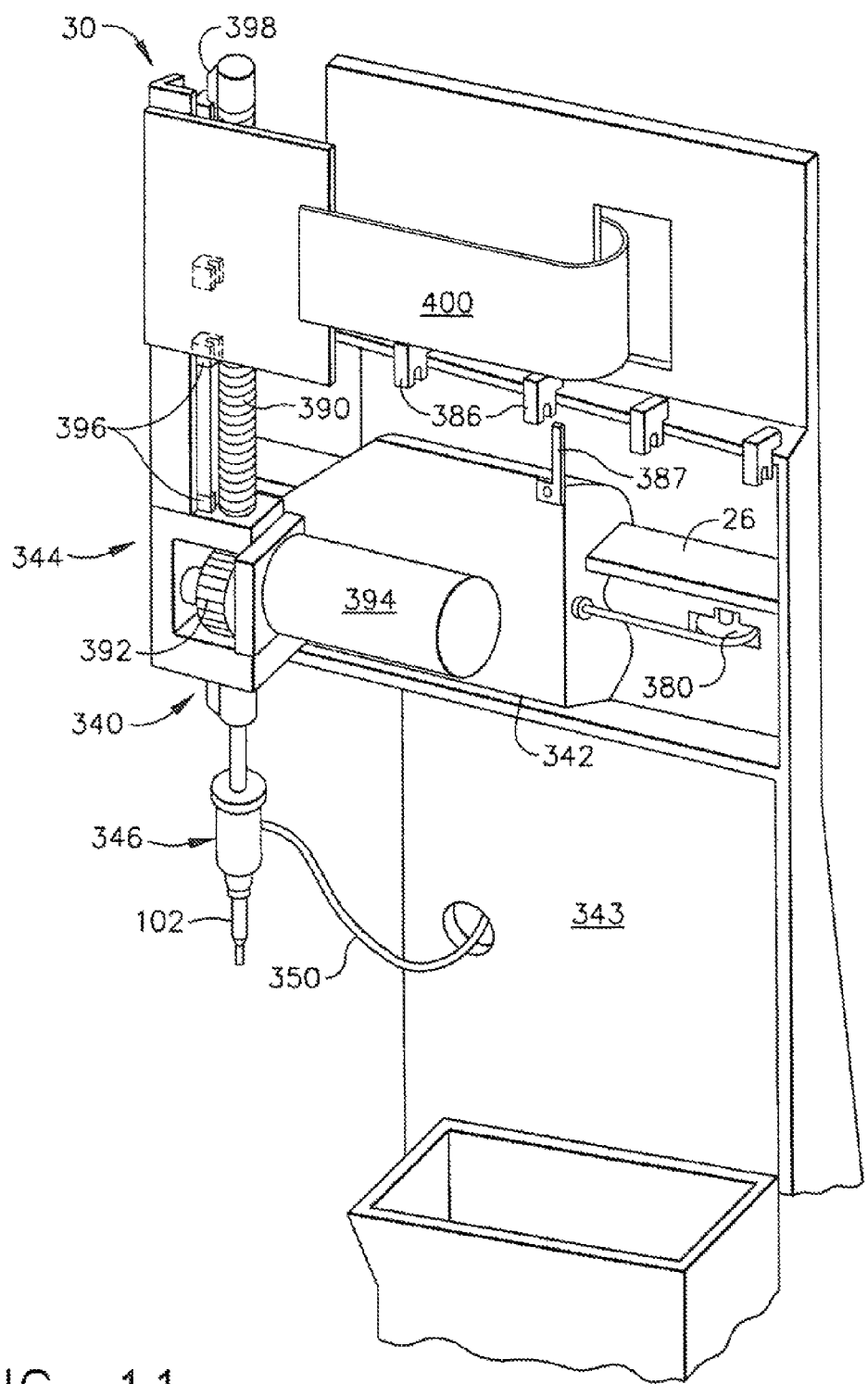
FIG. 11 is a perspective view of a metering system for the analyzer of FIG. 1 showing a dispenser and a carriage.
Figure 12:
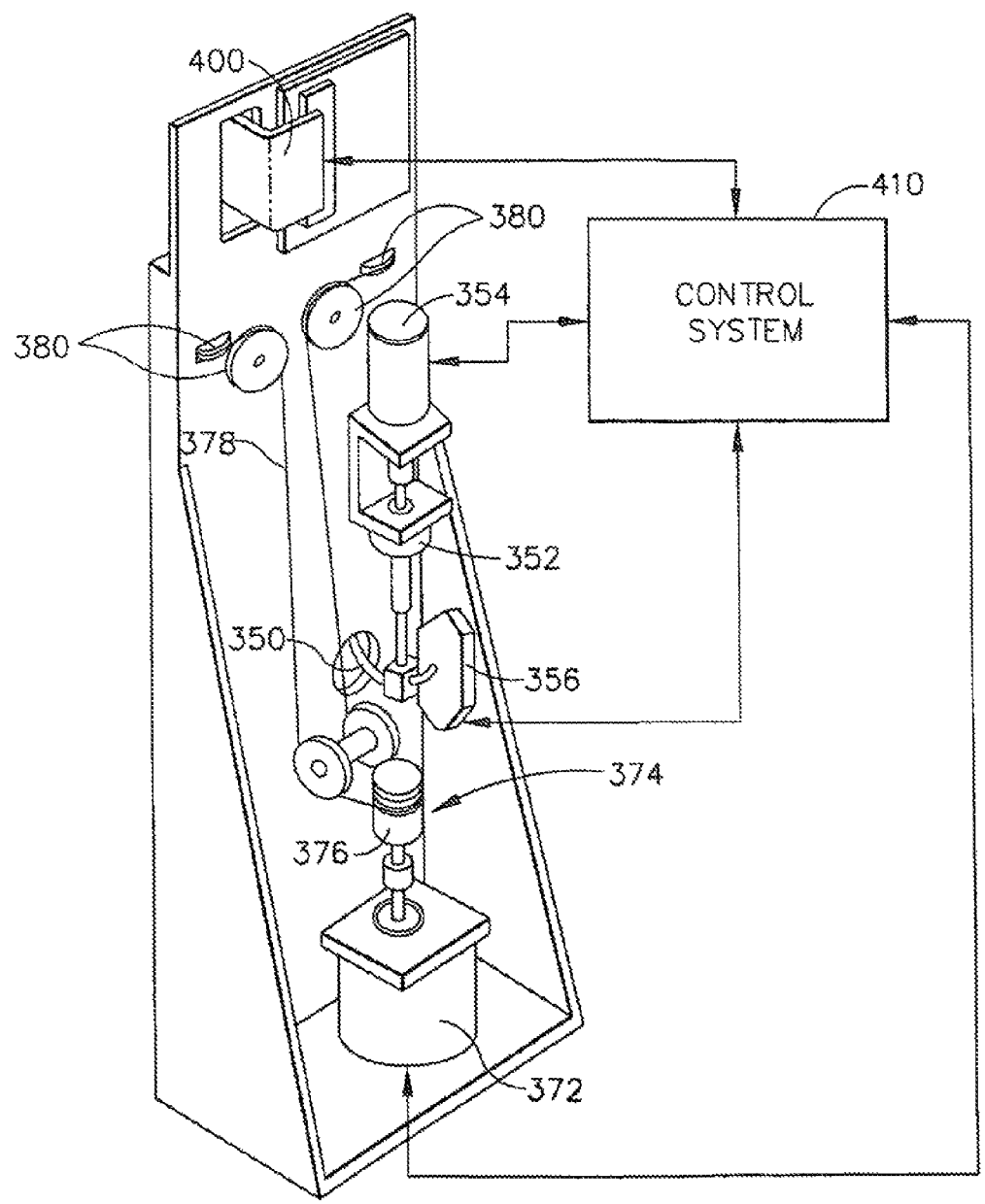
FIG. 12 is a perspective view of a pump for the dispenser and a drive mechanism for the carriage operatively connected to a control system for performing a calibration and automatic alignment method.

With reference to FIG. 11, metering truck 30, 44 comprises a dispenser 340 and a means for positioning dispenser 340 which includes a carriage 342 for moving dispenser 340 laterally through a plurality of stations (P1 through P13 as shown in FIG. 1) in analyzer 10, and a vertical drive 344 for raising and lowering dispenser 340 at each of the stations P1 through P13. Dispenser 340 comprises a dispenser head 346 which is adapted to receive disposable metering tip 102, and is connected by means of a line 350 to a pump 352 (FIG. 12) of the positive displacement type. Pump 352 comprises a piston, not shown, which is driven by a bi-directional stepper motor 354. The stepper motor 354 is operatively connected to and controlled by a control system 410.

When motor 354 is actuated by the control system 410 in one direction, a partial vacuum is created in line 350 by pump 352, and fluid is drawn into tip 102 until the tip is partially filled. Motor 354 is actuated in an opposite direction to meter fluid from tip 102. In the metering operation, motor 354 drives pump 352 for a pre-selected period during which the pressure in line 350 and tip 102 is raised sufficiently to force about 10 ul of fluid onto an analysis slide. Under certain operating conditions, depending on the amount of fluid aspirated into tip 102, it may be desirable to vent line 350 before dispensing fluid onto an analysis slide. A pressure transducer 356 is operatively connected to and controlled by control system 410 and closely monitors pressure in line 350 for purposes which will be explained in more detail hereinafter.

Carriage 342 is mounted for horizontal movement on metering transport rail 26. Rail 26 is carried on a pylon 343 attached to the analyzer frame, not shown. A drive means for carriage 342 includes a bi-directional stepper motor 372 (FIG. 12) which is connected to a capstan drive 374. Drive 374 comprises a drum 376; a cable 378 carried on drum 376 is supported on guide pulleys 380 and connected to carriage 342. The stepper motor 372 is operatively connected to and controlled by the controller 410. It will be seen from FIGS. 11 and 12, that when motor 372 is driven, for example, in a counterclockwise direction, as viewed in FIG. 12, carriage 342 will move to the right (FIG. 11). Carriage 342 must be located along a line at multiple points or stations which include for example, stations at positions P1 through P13. Horizontal-position sensors 386 of a photoelectric type cooperate with a carriage flag 387 on carriage 342 to precisely position the carriage 342 at each of these stations P1 through P13.

Vertical drive 344 comprises a rack 390 which is attached to dispenser head 346. Rack 390 is raised and lowered by means of a pinion 392 driven by a stepper motor 394 mounted on a carriage 342. Vertical-position sensors 396 cooperate with a rack flag 398 on rack 390 to precisely determine the vertical position of dispenser head 346. Power from a power supply, not shown, is supplied to the sensors 396 and motor 394 through a ribbon cable 400. The sensors 396 and motor 394 are operatively connected to and controlled by the controller 410 through the ribbon cable 400.

In the use of the disclosed metering mechanism 22 and 42 with the high-throughput clinical analyzer 10, as shown in FIG. 1, a metering operation takes place approximately every nine (9) seconds. Thus, it will be seen that each of the steps in the metering cycle must be carefully controlled and monitored by the control system 410, and metering apparatus 30 and 44 must function in timed relation to other elements of analyzer 10. Pressure transducer 356 is used to monitor the performance of apparatus 30 and 44. Pressure is sensed in line 350, and if conditions are present such as a plugged tip 102, no fluid in sample container 18, or a separation of the fluid stream between the tip 102 and the slide element 36, or if the tip 102 is close to a surface, they will be detected by the pressure transducer 356. The control system 410 for the metering apparatus 30 and 44 includes one or more computers which may take any of the various forms known in the art that include programmable microcomputers. In general, the instructions and method of programming such computers is well known in the art, and thus, no further explanation is considered necessary.

The metering truck 30 carrying the unsealed metering tip 102 with aspirated sample is shuttled along the transport rail 26 from the primary sample handler 14 to the metering station 68. At the metering station 68, a volumetric portion of patient sample contained within the metering tip 102 is dispensed onto a dry slide element, shown pictorially as 36 in FIG. 1, which is arranged to be loaded using conventional means, such as a reciprocating pusher blade 39, also shown pictorially in FIG. 1, into the first incubator assembly 34. The sample which is metered is then used in conjunction with the dry chemistry system of the herein described combinational analyzer 10. The sample is metered onto, for example, a calorimetric or potentiometric slide element which is incubated, the sample being analyzed at a read station for correlated analyte detection. Details relating to the incubation and testing of dry slide elements is known in the field such as described, for example, in U.S. Pat. No. 4,296,069 entitled: Apparatus for Processing an Analysis Slide, and therefore require no further discussion.

Following the above-described metering step, the metering tip 102 is then further shuttled by the metering truck 30 toward the sample aliquot handler 40 and more specifically to the tip sealer 142. At the tip sealer 142, the metering tip 102 is placed within the opening 182 of the sealer housing 174 and is lowered until the tip is positioned relative to the anvil 186. Heat from the heating element 190 is applied through the anvil 186 to the dispense end 105 of the tip 102 while the tip is still attached to the proboscis (not shown) of the metering truck 30. The fluid within the tip 102 is aspirated further away from the dispense end 105 and a bubble is formed which prevents temperature effects to the fluid as well as removing the fluid from the area to be sealed. As noted above, further details relating to the above noted sealing operation are provided in previously incorporated commonly owned U.S. Pat. No. 6,797,518, issued Sep. 28, 2004, of Jacobs et al., entitled ANALYSIS METHOD WITH SAMPLE QUALITY MEASUREMENT.

The above sealing operation seals the dispense end 105 of the metering tip 102, FIG. 9, 10, and therefore creates a sample supply container for use by the wet chemistry system of the present combinational analyzer 10 as will be described below.

Following the above sealing steps, the proboscis (not shown) is raised in a conventional manner, removing the metering tip 102 from the tip sealer 142. The metering tip 102 is then shuttled along the transport rail 26 by the metering truck 30 to the tip stripping assembly 154 which is provided on the cover 84 of the sample aliquot handler 40. The opening 162 of the tip stripping assembly 154 is aligned with the transport rail 26 and more specifically the travel path of the metering truck 30. The proboscis (not shown) is lowered along with the attached metering tip 102, FIG. 9, into the opening 162 of the raised portion 206 of the cover 84. Initially, the dispense end 105 of the sealed metering tip 102, FIG. 9, 10, engages the ramped surfaces 220 of the V-blocks 214. As the proboscis is further lowered, the downward force applied by the tip 102 against the ramped surfaces 220 causes the gap between the V-blocks to widen and permits the entire metering tip 102 to pass through the extended gap. When the top of the upper end 103 of the metering tip 102 has passed through the V-blocks 214, the V-blocks are caused to close inwardly due to the biasing force applied by each of the compression springs 218 toward the body of the proboscis, above the top of the metering tip 102. Upward movement of the proboscis therefore causes engagement against the shoulder of the open upper end 103 of the metering tip 102, causing the tip to be stripped from the proboscis and dropped into an empty sample container supply position 100 of the circular ring 96 of the inner rotor assembly 88.

A tip presence sensor located at a dump position of the sample aliquot handler 40 indicates whether or not a sample container supply station 100 is empty prior to loading the sealed metering tip 102, the sensor further confirming the presence of a new tip which has been loaded.

The above noted steps are repeated in order that a plurality of sealed metering tips 102 are individually added to the sample aliquot handler 40 and more specifically to sample container supply stations 100 of the inner rotor assembly 88. The rotatable ring 96 of the inner rotor assembly 88 is driven about its axis of rotation through means of the meshing of the engagement portion 130 of the drive motor and the gear teeth 134 provided on the ring 96 either incrementally or as required. The retained sample containers (sealed metering tips 102) are driven relative to an aspiration station 158 and sample integrity read station 234. According to the present embodiment, the sample integrity read station is angularly disposed between the tip stripping assembly 154 and the aspiration station 158. The locations of each of the above stations 158, 234 can of course be suitably varied. What should be noted is that the disposition of the sample integrity station 234 within the housing of the sample aliquot handler 40 permits readings to be performed at a time which does not affect throughput of the analyzer 10.

As more clearly shown in FIGS. 9 and 10, a sealed metering tip 102 is advanced by the inner rotor assembly 88, FIG. 3, to the sample integrity station 234. As noted previously, the sample integrity read station 234 is placed at a predetermined circumferential position relative to the sample container supply positions 100 of the rotatable ring 96. At this station 234 and according to his embodiment, the sealed metering tip 102 is roughly angularly aligned with the test cavity 239 and moreover is roughly vertically aligned with the receiving and transmitting optics 236, 238 of the optical testing device in the position which is shown in FIG. 10.

The optical reading apparatus according to this embodiment, is a spectrophotometer which makes light absorbance transmission measurements of a sample retained within the sealed disposable metering tip 102. The sealed metering tip 102, being made from a transparent plastic material therefore permits optical testing to be performed upon the fluid contents. Details relating to the optical reading of the fluid contents of the sample are known as provided in U.S. Pat. Nos. 6,013,528 and 5,846,492, to Jacobs et al., the entire contents of each being hereby incorporated by reference.

According to this embodiment, the lift mechanism is used to better or repeatably align each sealed metering tip 102 to the receiving and transmitting optics 236, 238 of the optical testing apparatus. The actuator 244 is initially engaged and the tip receiving cavity 250 of the engagement member 248 of the linear actuator 244, sized to receive the dispense end 105 of the tip 102, causes the tip to be moved upwardly relative to its position within the ring 96 (the ring is not shown in FIGS. 9 and 10). The upward movement of the sealed metering tip places the lower portion of the tip containing the aliquot of sample fluid into proper alignment between the receiving and transmitting portions 236, 238 of the optical testing device prior to obtaining readings of the contained aliquot sample. The flag 252 provided on the engagement member 248 is used to perform a dark read of the optical reading apparatus prior to lifting the metering tip 102, as better described by the above incorporated Jacobs patents.

Upon completion of the read, the engagement member 248 is lowered and the metering tip is again lowered into engagement within the outer slotted opening 104 of the corresponding sample container supply position 100. The ring 96 of the inner rotor assembly 88 resumes rotational movement by means of its gear drive mechanism until the metering tip 102 is aligned with the opening representing the aspiration station 158. If sample is required, the secondary metering system 42 is used to bring a micro-tip (not shown) from the micro-tip loader 58 using a proboscis (not shown) extending downwardly from the movable metering truck 44 which is moved into position using the metering transport rail 26. The operation of the secondary metering mechanism in terms of the attachment of a tip to the proboscis (not shown), the raising and lowering of the proboscis relative to the metering truck 44, the movement of the metering truck along the transport rail 26 and the aspiration and dispensing of fluid using the micro-tip are literally identical to that of the primary metering mechanism 22, FIG. 1 and those details in and of themselves require no further discussion. As previously defined, however, the micro-tip 107 is a fluid dispensing member which can fit within the confines of a sealed metering tip 102, permitting aspiration therefrom.

The micro-tip 107 is positioned within the confines of the sealed metering tip 102 in order to aspirate a predetermined volume of liquid from the sealed tip to use the liquid to conduct a wet assay or dilution. The metering truck 44 then moves the micro tip into alignment with a reaction vessel 64 and dispenses the aspirated fluid. Following the delivery of patient sample aspirated from the secondary sample container, the micro tip is disposed of by dropping the used micro-tip into a dump station (not shown) of the analyzer 10.

In a clinical analyzer, reagents are also brought to the reaction vessel 64 from a reagent container 54 which is rotated to an aspiration position by the reagent wheel 52. In one aspect, a mainframe metering tip 102 is first picked up by the metering truck 44 from the outer ring of the sample aliquot handler apparatus 40 and is then shuttled to the aspiration position of the reagent wheel 52. Reagent fluid is then aspirated from the reagent container 54 into the attached metering tip 102. The used metering tip 102 is then shuttled along the metering rail 26 to the metering position and the reagent is dispensed directly into the reaction chamber of the reaction vessel 64. Preferably, the reaction chamber of the vessel 64 is sized to receive the tip 102, whose dispense end 105 can be positioned within the confines of the reaction vessel and more particularly placed into direct contact with the already retained sample/reagent. As reagent is dispensed, the fluids are "swish-mixed" providing an advantage over metering systems which require a paddle or other apparatus for mixing.

Following the above dispensing step, this tip 102 is also sealed and discarded at the dump station. Preferably, the coordination of wet assay testing utilizes the sample aliquot handler apparatus 40 as part of the scheduling in order to effectively utilize throughput. Additional quantities of a second reagent and/or sample or other substances such as calibration liquid can be obtained similarly using an unused metering tip which is picked up by the movable truck 44 of the secondary metering system 42 shuttled to an aspiration station for aspiration of an appropriate liquid and then dispensing the liquid into the reaction vessel. As such, there is no need to wash the reagent proboscis since the liquid is retained by the metering tip. In this analyzer, the use of disposable metering tips effectively replaces the wash apparatus normally associated with so-called wet chemistry systems. It should be noted that the sequencing of fluids (sample followed by first reagent followed by second reagent) may not be essential relative to the workings of the analyzer. That is, and in the majority of wet assays, first reagent is first metered into the reaction vessel 64 prior to the dispensing of sample.

Details relating to the operation of the wet chemistry portion of the herein described analyzer are provided in commonly owned U.S. patent application Ser. No. 10/185,613, published as Pub. No. US 2003/0022380 on Jan. 30, 2003, of Jakubowicz et al. entitled "Chemistry System for a Clinical Analyzer" and commonly owned U.S. patent application Ser. No. 09/910,399, published as Pub. No. US 2003/0026733 on Feb. 6, 2003, of LaCourt et al. entitled "Auxiliary Sample Supply for a Clinical Analyzer", the entire contents of each of which are herein incorporated.

Once the sealed metering tip 102 has been used in accordance with all tests/assays which may be required based on the scheduling of the combinational analyzer 10, the ring 96 of the inner rotor assembly 88 is rotated into alignment with the tip removal assembly 122. At this location, an actuable hook blade 124 which is moved outwardly by the assembly engages the protruding upper end 103 and body of the metering tip 102 and pulls the tip from the slotted outer opening 104 of the supply station 100 to the larger diameter inner opening 108. The inner opening 108 of the sample container supply stations 100 has a diameter which is larger than that of the upper end 103 of the tapered metering tip 102, thereby causing the tip to fall through the opening and into a dump station (not shown) located beneath the ring 96. A position sensor 128 detects the position of the hook blade relative to the inner rotor assembly 88.

Method for Normalizing Surface Tension

The above description describes a combinational clinical analyzer having a dry and wet chemistry system. The method of the subject invention relates to the wet chemistry system of this or a similar analyzer. In particular, the method provides for the treatment of the sample fluid with a surface tension-normalizing agent without adulterating the entire sample fluid and without substantially reducing throughput of the analyzer. This is accomplished by the following components/ steps which incorporate into the analyzer/method as described above.

A metering tip 102 aspirates 180 μl of sample fluid from a sample container 18. The metering tip 102 is positioned and moved by the primary metering mechanism 22. As discussed above, the metering tip 102 is then shuttled to the tip sealer 142. Once sealed the metering tip 102 forms a cuvette or cuvatip containing the aliquot or portion of the sample fluid. This sealed metering tip 102 is placed in an empty sample container supply position 100 of the sample aliquot handler 40. The secondary metering mechanism 42 then picks up a micro-tip 107 and proceeds to the reagent wheel 52 where a reagent container 54 contains the surface tension-normalizing agent. The micro-tip 107 is "coated" or pre-treated with the surface tension-normalizing agent by aspirating 120 μl of the agent into the micro-tip, and metering or dispensing 100 μl back out of the micro-tip. The remaining 20 μl of surface tension-normalizing agent is then transported to the metering tip 102 that has previously been sealed, situated on the sample aliquot handler 40, and which contains the aliquot or portion of the sample fluid. The secondary metering mechanism 42 meters the 20 μl of agent into the metering tip 102, then proceeds to aspirate 120 μl of the resulting mixture into the micro-tip 107 and then meters 120 μl out of the micro-tip 107, repeating this aspirate/meter step three times. The resulting mixture in the metering tip 102 is a homogeneous mixture of sample fluid and surface tension-normalizing agent, having a normalized surface tension. This mixture is then used for testing on the clinical analyzer, in particular the wet chemistry system. As such, a second micro-tip 107 is used to aspirate an aliquot or portion of the mixture, and that aliquot or portion of the mixture is transported by a metering mechanism to the reaction vessel 64 where the mixture is analyzed as required.

This method is particularly useful when the sample fluid contains analytes of interest that are hydrophobic. Such analytes stick to the plastic material of which the tips are constructed, causing inaccurate results in the measurement of the analyte. The mixing of the surface tension-normalizing agent with the fluid sample, using the resulting mixture for analysis, blocks this adhesion of the analyte to the plastic material allowing accurate and true measurement of the analyte present in the sample fluid. The mixing also improves metering performance of the clinical analyzer.

The method of the subject invention permits the use of disposable plastic tips with "sticky" analytes and with the use of extremely small sample volumes where accurate metering can be a problem. This is accomplished by treating only a portion or aliquot of the original sample fluid, leaving the original sample fluid for other testing on other analyzers as is often required in the field. Furthermore, the addition of the surface tension-normalizing agent is accomplished in an automated manner using the existing analyzer components with no substantial decrease in throughput of the analyzer. This is another advantage in the field.

Thus, the invention provides a method of normalizing surface tension of a sample fluid on a clinical analyzer, the method comprising:

aspirating a portion of a sample fluid into a metering tip, the metering tip having a lower end through which the sample fluid is aspirated and an upper end;

sealing the lower end of the metering tip, forming a cuvette for the portion of the sample fluid;

pre-treating a micro-tip with a surface tension-normalizing agent, and then dispensing the surface tension-normalizing agent into the sample fluid in the cuvette;

mixing the surface tension-normalizing agent and the sample fluid in the cuvette using the micro-tip to create a mixture of the sample fluid and the surface tension-normalizing agent, the mixture having a normalized surface tension; and using the mixture for testing on the clinical analyzer.

Preferably, the surface tension normalizing agent is a surfactant, such as a non-ionic surfactant. Suitable non-ionic surfactants include poly(oxyalkylene) block copolymers of the formula $(PO)_Y(EO)_X(PO)_Y$, wherein PO is polypropylene oxide, EO is polyethylene oxide, and X<Y. A preferred poly (oxyalkylene) block copolymers is Pluronic 25R2® wherein X is 14 and Y is 22. Other suitable non-ionic surfactants include polyalkoxylated alkanols. A preferred polyalkoxylated alkanol is ceteareth 55, sold by BASF under the name Plurafac A39®. A presently preferred embodiment is a mixture of Pluronic 25R2® and Plurafac A39®. Suitable non-ionic surfactants also include polyethylene glycol P-1,1,3,3-tetramethylbutylphenyl ether (commonly known as TX-100®).

Table 1 shows the various surfactants/compounds which were tested for the ability to normalize surface tension and/or block adhesion of analytes to the plastic micro-tips, including various combinations thereof.

In analyses for drugs of abuse (DAT), the sample is preferably urine. In such a case, the method of the subject invention is particularly useful in the analysis for a hydrophobic molecule, such as a tetrahydrocannabinoid or a tetrahydrocannabinoid metabolite, or methadone.

While particular embodiments of the invention have been shown, it will be understood, of course, that the invention is not limited thereto, since modifications may be made by those skilled in the art, particularly in light of the foregoing teachings. Reasonable variation and modification are possible within the scope of the foregoing disclosure of the invention without departing from the spirit of the invention.

TABLE 1

| Surfactants/ Components Tried | Classification | HLB[1] | Surfactant Concentration (final) | Recovery %[2] (MC707) |
|---|---|---|---|---|
| Surfactants | | | | |
| Nothing Added | NA | | NA | 58 |
| Water | NA | | 0.074% | 53 |

TABLE 1-continued

| Surfactants/Components Tried | Classification | HLB[1] | Surfactant Concentration (final) | Recovery %[2] (MC707) |
|---|---|---|---|---|
| N-lauroyl sarcosine | anionic | | 0.074% | 77 |
| LADO (lauryldimethylamine oxide) | zwitterionic | | 0.074% | 65 |
| SDS | anionic | | 0.074% | 74 |
| C12APS (Zwittergent 3-12) | zwitterionic | | 0.074% | 77 |
| Zwittergent 3-16 | zwitterionic | | 0.074% | 70 |
| Chondroitin sulfate | proteoglycan | | 0.074% | |
| TX-100 | non-ionic | 13.5 | 0.074% | 78 |
| Tween 20 | non-ionic | 16.7 | 0.074% | 72 |
| C16 TAB | cationic | | 0.074% | 57 |
| Brij 35 | non-ionic | 16.9 | 0.074% | 60 |
| Plurafac A39 | non-ionic | 24 | 0.100% | Note 3 |
| Pluronic 25R2 | non-ionic | 6 | 0.100% | Note 4 |
| Plurafac A39/Pluronic 25R2 (PA39/P25R2) | non-ionic/non-ionic | | 0.074% total (2:3 ratio) | 74 |
| Surfactants and Solvents | | | | |
| 5% DMSO, 0.045% NaCl | solvent/salt | | NA | 49.5 |
| 5% EtOH | solvent | | NA | 49.2 |
| 5% DMSO, 0.045% NaCl, 0.1% TX-100 | solvent/salt/non-ionic | | 0.100% | 78.7 |
| 5% DMSO, 0.045% NaCl, 0.1% PA39/P25R2 | solvent/salt/non-ionic | | 0.100% | 88.1 |
| 5% EtOH, 0.045% NaCl, 0.1% TX-100 | solvent/salt/non-ionic | | 0.100% | 86.1 |
| 5% EtOH, 0.045% NaCl, 0.1% PA39/P25R2 | solvent/salt/non-ionic | | 0.100% | 85.4 |
| 5% MeOH, 0.045% NaCl, 0.1% TX-100 | solvent/salt/non-ionic | | 0.100% | 83.9 |
| 5% MeOH, 0.045% NaCl, 0.1% PA39/P25R2 | solvent/salt/non-ionic | | 0.100% | 78.1 |
| 5% IPA, 0.045% NaCl, 0.1% TX-100 | solvent/salt/non-ionic | | 0.100% | 86.6 |
| 5% IPA, 0.045% NaCl, 0.1% PA39/P25R2 | solvent/salt/non-ionic | | 0.100% | 86.4 |
| Final Patch | | | | |
| TX-100 | | | 0.074% | 71.8 |
| TX-100 | | | 0.100% | 78.2 |
| TX-100 | | | 0.200% | 73.1 |
| TX-100 | | | 0.250% | 83.4 |
| PA39/P25R2 | | | 0.074% | 81.1 |
| PA39/P25R2 | | | 0.100% | 82.4 |
| PA39/P25R2 | | | 0.200% | 77.5 |
| PA39/P25R2 | | | 0.250% | 83.2 |

[1] HLB = hydrophile/lipophile balance. This number is frequently used to characterize non-ionic polyoxyethylenes.
[2] The % recovery is calculated assuming a nominal concentration of 100 ng/mL for BCD control MC707.
[3] Did not work as well alone as in combination with P25R2
[4] Did not work as well alone as in combination with PA39

The invention claimed is:

1. A method of normalizing surface tension of a sample fluid on a clinical analyzer, the method comprising:

first aspirating a portion of a sample fluid into a metering tip, the metering tip having a lower end through which the sample fluid is aspirated and an upper end, and the sample fluid being free of surface-tension normalizing agent;

then sealing the lower end of the metering tip, forming a cuvette for the portion of the sample fluid;

then pre-treating a micro-tip with a surface tension-normalizing agent by aspirating a volume of a surface-tension normalizing agent into the micro-tip, then dispensing out a portion of the volume of the surface-tension normalizing agent and retaining in the micro-tip a remaining portion of the volume of the surface-tension normalizing agent;

then dispensing the remaining portion of the volume of the surface tension-normalizing agent into the sample fluid in the cuvette;

then mixing the remaining portion of the volume of the surface tension-normalizing agent and the sample fluid in the cuvette using the micro-tip to create a mixture of the sample fluid and the surface tension-normalizing agent, wherein the mixing comprises repeatedly aspirating and dispensing a volume of the mixture, the volume of the mixture being less than or equal to the volume of the surface-tension normalizing agent used to pre-treat the micro-tip, the mixture having a normalized surface tension; and using the mixture for testing on the clinical analyzer.

2. The method of claim 1 wherein portions of the mixture for testing are aspirated from the cuvette to a reaction vessel using a second micro-tip and wherein the surface tension-normalizing agent blocks adhesion of analytes present in the mixture to the second micro-tip.

3. The method of claim 1 wherein normalizing surface tension also improves metering performance of the clinical analyzer.

4. The method of claim 1 wherein the surface tension-normalizing agent is a surfactant.

5. The method of claim 4 wherein the surfactant is a non-ionic surfactant.

6. The method of claim 5 wherein the non-ionic surfactant is a poly(oxyalkylene) block copolymer of the formula $(PO)_Y(EO)_X(PO)_Y$, wherein PO is polypropylene oxide, EO is polyethylene oxide, and X<Y.

7. The method of claim 6 wherein the poly(oxyalkylene) block copolymer is Pluronic 25R2®, wherein X is 14 and Y is 22.

8. The method of claim 5 wherein the non-ionic surfactant is a polyalkoxylated alkanol.

9. The method of claim 8 wherein the polyalkoxylated alkanol is ceteareth 55 (Plurafac A39®).

10. The method of claim 1 wherein the surface tension-normalizing agent agent is a mixture of Pluronic 25R2® and Plurafac A39®.

11. The method of claim 1 wherein the surface tension-normalizing agent is polyethylene glycol P-1,1,3,3-tetramethylbutylphenyl ether (TX-100®).

12. The method of claim 1 wherein the sample is urine.

13. The method of claim 1 wherein the sample fluid is being analyzed for a hydrophobic molecule.

14. The method of claim 13 wherein the hydrophobic molecule is a tetrahydrocannabinoid or a tetrahydrocannabinoid metabolite.

15. The method of claim 13 wherein the hydrophobic molecule is methadone.

* * * * *